United States Patent [19]

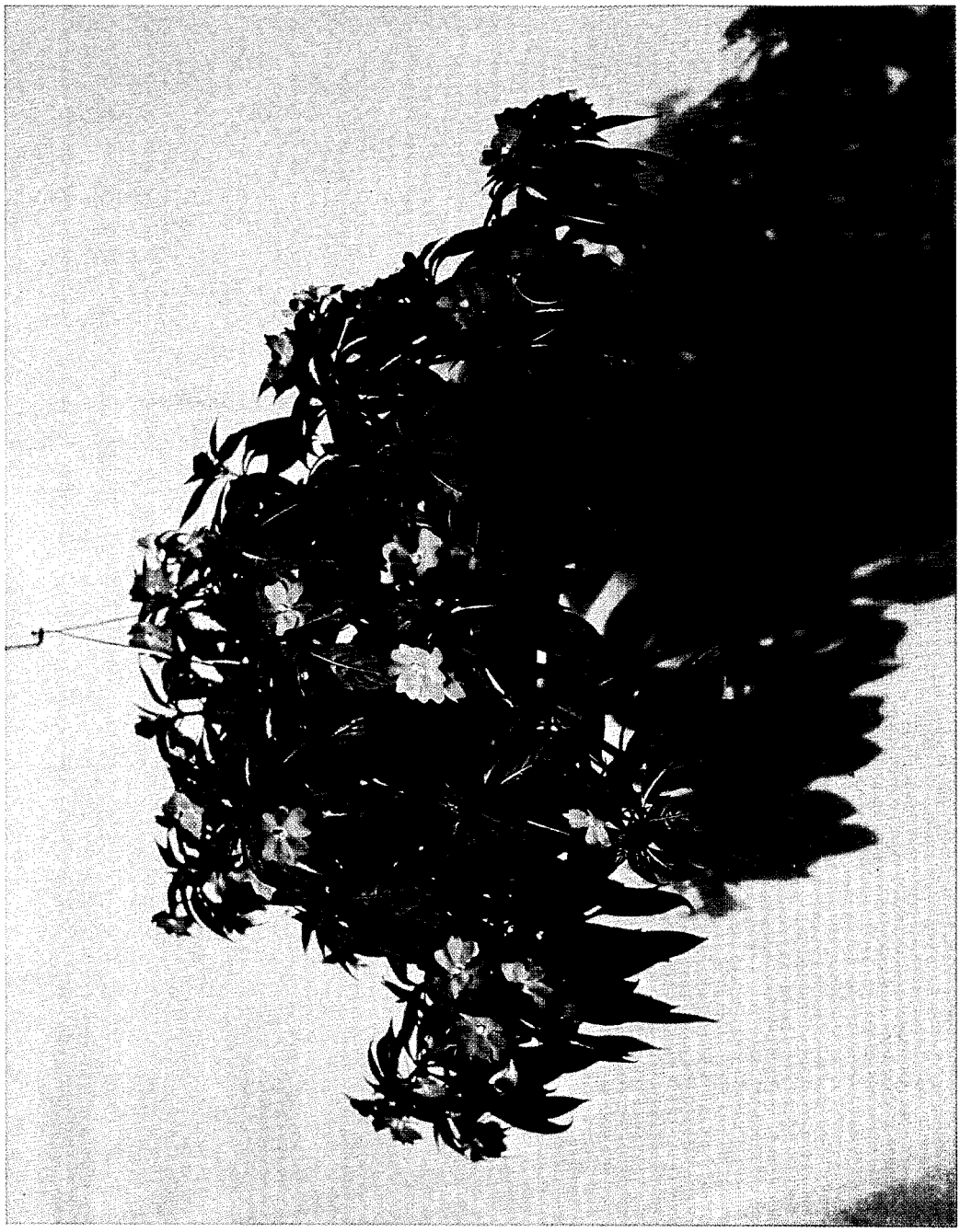

Ryan

[11] Plant 4,193

[45] Jan. 17, 1978

[54] IMPATIENS PLANT—AZTEC

[76] Inventor: John J. Ryan, 39877 Sundale Drive, Fremont, Calif. 94538

[21] Appl. No.: 782,282

[22] Filed: Mar. 28, 1977

[51] Int. Cl.[2] ..... A01H 5/00
[52] U.S. Cl. ..... Plt./68
[58] Field of Search ..... Plt./68

*Primary Examiner*—Robert E. Bagwill
*Assistant Examiner*—James R. Feyrer
*Attorney, Agent, or Firm*—James R. Cypher

[57] ABSTRACT

This invention relates to a new and distinct variety of New Guinea Impatiens plant known by the cultivar name Aztec, and discovered by me in commercial greenhouses in Fremont, Calif. Aztec is closest in characteristics to existing Mikkel Red Coat but is particularly characterized by a distinctive clean-cut variegation; excellent breaking action; a dark yet bright red flower with a white eye, usually ringed with a bluish tint; flowers well with good duration; and makes a very good basket plant and productive stock plant.

1 Drawing Figure

BACKGROUND OF THE INVENTION

The present new variety (seedling 76-10-2) was discovered by me in a commercial greenhouse in Fremont, Calif. as a result of the cross pollination of unpatented pistil parent 75-4 and unpatented pollen parent 75-24.

Asexual reproduction of my new cultivar by terminal or stem cuttings grown in hanging baskets in a plastic (polyethylene) greenhouse in Fremont, Calif. under normal environmental conditions show that the characteristics described come true to form and are established and transmitted through succeeding propagations.

Color readings were taken during daylight hours in full sun, and all colors are based on the Royal Horticultural Society Colour Chart.

BRIEF SUMMARY

Aztec is closest in characteristics to the existing Mikkel Red Coat.

The following outstanding characteristics of Aztec distinguish it from the existing Mikkel Red Coat:

1. Excellent contrast of variegation to flower color.
2. Excellent breaking action, making a good basket and a very productive stock plant.
3. Flowers well in quantity and duration.
4. Flower is bright yet dark red with a white eye, usually ringed with a bluish tint, and is much darker than the existing Mikkel Red Coat.
5. The distinct clean-cut variegation is a bright cream yellow surrounded by a bright green, unlike the poor contrast of the Mikkel Red Coat.
6. Is a faster grower than Mikkel Red Coat.

DESCRIPTION OF THE PHOTOGRAPH

The accompanying colored photograph illustrates the overall appearance of the cultivar Aztec showing the color as true as reasonably possible for this type of colored reproduction. However, under low light and cool temperatures the flower color darkens. Under high light the variegation width increases and becomes more distinctive and clean-cut.

DETAILED DESCRIPTION

The following detailed description of Aztec is based on observations made of the new cultivar on Jan. 13, 1977.

PLANT

Name: Aztec.
Origin: Seedling 76-10-2 of the cross pollination of unpatented pistil parent 75-4 and unpatented pollen parent 75-24.
Form: Generally spreading.
Height to flowering: 15 to 30 cm.
Growth: Fast.
Type of cutting: Terminal or stem.
Rooting time: Typical, 10 to 14 days.
Rooting habit: Typical, fast, dendritic.

FOLIAGE

Arrangement: Lower leaves opposite (usually one set), upper foliage of any shoot generally whorls of 4-7.
Shape: Elliptic.
Tip: Acuminate.
Base: Attenuate.
Margin: Ciliate at the base to serrulate at tip.
Venation: Pinnate.
Size:
- *Petiole and blade.*—11 cm.
- *Length of blade.*—9 cm.
- *Width at widest point of fully expanded, mature leaf.*—3.5 cm.

Surface:
- *Smoothness.*—Slight external crinkle.
- *Texture.*—Glabrous, typically waxy.

Variegation: Light heavily influences the width of the variegation. High light also makes the variegation more clean-cut.
Color:
- *Petiole.*—Upper 47C, lower 48D.
- *Veins.*—3A.
- *Leaf.*—Upper: 136A; Lower: 138B.
- *Variegation.*—Edge: 154A; Middle: 1A; Center: 3A.

STEM

Color: Mature stem 47B, upper stem light red but green at nodes.
Internode:
- *Length.*—Moderate.
- *Size.*—Small to moderate.

Node expanded (relative to internode): Moderately expanded.

Breaking action: Excellent.

FLOWER

Form: Typical.

Borne: End of branches, terminal.

Blooming habit:

*Relative number.*—Profuse.

*Time to flower.*—After 3–6 nodes.

*Longevity.*—Approximately 5 days (heavily dependent on temperature).

Size of mature flower: First flower on a plant may be small.

*Length.*—4.0 cm.

*Width.*—4.0 cm.

*Spur.*—5.0 to 5.5 cm.

Color: Lighter red under high light.

*Eye.*—White portion 155D to blue-red 68A.

*Middle.*—45B.

*Edge.*—45B, sometimes shows bluish halo.

*Pedicel.*—51B.

REPRODUCTIVE ORGANS

Stamen:

| | |
|---|---|
| STAMEN: | |
| Anthers | typical in form but smaller, fused hood over pistil |
| Filaments | |
| Pollen: | |
| Color: | 158B |
| Abundance: | Typical, plenty |
| PISTILS: | |
| Stype | typical in form, but smaller |
| Ovaries | |

OTHER CHARACTERISTICS

Diseases: Aztec is no more susceptible than other Impatiens varieties to most soft rots.

Insects: Aztec has equal or greater resistance to spider mites than most varieties on the market.

I claim:

1. A new and distinct form of Impatiens as described and illustrated known by the cultivar name Aztec, and particularly characterized by a distinctive clean-cut variegation; excellent breaking action; a dark, yet bright red flower with a white eye, usually ringed with a bluish tint; flowers well with good duration; and makes a very good basket plant and productive stock plant.

* * * * *

UNITED STATES PATENT AND TRADEMARK OFFICE

CERTIFICATE OF CORRECTION

PATENT NO. : PP 4,193

DATED : January 17, 1978

INVENTOR(S) : John J. Ryan

It is certified that error appears in the above-identified patent and that said Letters Patent are hereby corrected as shown below:

Column 4, line 20, after the word Impatiens should read --- plant ---

Signed and Sealed this

*Nineteenth* Day of *June 1979*

[SEAL]

*Attest:*

RUTH C. MASON
*Attesting Officer*

DONALD W. BANNER
*Commissioner of Patents and Trademarks*